(12) United States Patent
Vilsmeier et al.

(10) Patent No.: US 11,420,076 B2
(45) Date of Patent: Aug. 23, 2022

(54) UTILIZATION OF A TRANSPORTABLE CT-SCANNER FOR RADIOTHERAPY PROCEDURES

(71) Applicant: Brainlab AG, Munich (DE)

(72) Inventors: Stefan Vilsmeier, Munich (DE); Kajetan Berlinger, Munich (DE)

(73) Assignee: Brainlab AG, Munich (DE)

( * ) Notice: Subject to any disclaimer, the term of this patent is extended or adjusted under 35 U.S.C. 154(b) by 1328 days.

(21) Appl. No.: 15/534,049

(22) PCT Filed: Jun. 25, 2015

(86) PCT No.: PCT/EP2015/064376
§ 371 (c)(1),
(2) Date: Jun. 8, 2017

(87) PCT Pub. No.: WO2016/206743
PCT Pub. Date: Dec. 29, 2016

(65) Prior Publication Data
US 2017/0340902 A1 Nov. 30, 2017

(51) Int. Cl.
*A61N 5/10* (2006.01)
*A61B 6/00* (2006.01)
(Continued)

(52) U.S. Cl.
CPC .......... *A61N 5/1049* (2013.01); *A61B 6/032* (2013.01); *A61B 6/4405* (2013.01);
(Continued)

(58) Field of Classification Search
None
See application file for complete search history.

(56) References Cited

U.S. PATENT DOCUMENTS 6,666,579 B2 * 12/2003 Jensen .................... A61B 5/06
378/197
8,536,547 B2 9/2013 Maurer, Jr. et al.
(Continued)

FOREIGN PATENT DOCUMENTS

CN 1406117 A 3/2003
CN 101112316 A 1/2008
(Continued)

OTHER PUBLICATIONS

Kuriyama et al., "A New Irradiation Unit Constructed of Self-Moving Gantry-CT and Linac",Department of Radiation Oneology, University of Yamanashi, School of Medicine, Yamanashi, Japan, Aug. 28, 2002. 8 pages.
(Continued)

*Primary Examiner* — Shahdeep Mohammed
(74) *Attorney, Agent, or Firm* — Tucker Ellis LLP

(57) ABSTRACT

The present application relates to a data processing method for determining the position of a soft tissue body part within a patient's body. The data processing method includes acquiring CT-image data including information about the position of the body part within a coordinate system assigned to a transportable CT-device, wherein the patient's body is positioned relative to the treatment device, and wherein the CT-device is configured to be positioned relative to the patient's body and/or relative to the treatment device, acquiring first transformation data including information about a first transformation between the coordinate system assigned to the CT-device and a coordinate system assigned to the treatment device, and determining, based on the CT-image data and the first transformation data, position data including information about the position of the body part within the coordinate system assigned to the treatment device.

13 Claims, 3 Drawing Sheets

(51) Int. Cl.
  *A61B 6/03* (2006.01)
  *A61B 34/20* (2016.01)
  *A61B 90/00* (2016.01)

(52) U.S. Cl.
  CPC .......... *A61B 6/5217* (2013.01); *A61B 6/5235* (2013.01); *A61B 6/547* (2013.01); *A61N 5/1038* (2013.01); *A61N 5/1069* (2013.01); *A61B 2034/2051* (2016.02); *A61B 2034/2055* (2016.02); *A61B 2090/364* (2016.02); *A61B 2090/378* (2016.02); *A61N 2005/1051* (2013.01); *A61N 2005/1059* (2013.01); *A61N 2005/1061* (2013.01); *A61N 2005/1063* (2013.01)

(56) References Cited

U.S. PATENT DOCUMENTS

| | | | |
|---|---|---|---|
| 2002/0065461 A1* | 5/2002 | Cosman | A61B 90/16 600/426 |
| 2006/0215813 A1 | 9/2006 | Scherch et al. | |
| 2007/0053491 A1 | 3/2007 | Schildkraut et al. | |
| 2007/0153969 A1 | 7/2007 | Maschke | |
| 2008/0025459 A1 | 1/2008 | Shi et al. | |
| 2008/0260095 A1* | 10/2008 | Sukovic | A61B 6/08 378/20 |
| 2011/0301449 A1 | 12/2011 | Maurer, Jr. | |
| 2012/0008734 A1 | 1/2012 | Thomson et al. | |
| 2013/0085314 A1* | 4/2013 | Vilsmeier | G16H 70/20 600/1 |
| 2014/0049629 A1 | 2/2014 | Siewerdsen et al. | |
| 2016/0267659 A1* | 9/2016 | Vasey | G06T 15/08 |
| 2016/0278732 A1* | 9/2016 | Amiri | A61B 6/4441 |

FOREIGN PATENT DOCUMENTS

| | | |
|---|---|---|
| CN | 101247851 A | 8/2008 |
| CN | 103517737 A | 1/2014 |
| DE | 102006000837 A1 | 3/2007 |
| EP | 1389479 A1 | 2/2004 |
| WO | 2006/130659 A2 | 12/2006 |
| WO | 2006130659 A2 | 12/2006 |

OTHER PUBLICATIONS

Chinese Office Action for corresponding Chinese Application No. 201580071979.4, dated Mar. 18, 2019, 11 pages.

European Patent Office, Written Opinion of the International Searching Authority for corresponding PCT/EP2015/064376.

Kuriyama et al., A New Irradiation Unit Constructed of Self-Moving Gantry-CT and Linac, Int. J. Radiation Oncology Biol. Phys., vol. 55, No. 2, Feb. 1, 2003 (Feb. 1, 2003), pp. 428-435, XP055204870, DOI: P11 S0360-3016 (02) 03987-1.

* cited by examiner

UTILIZATION OF A TRANSPORTABLE CT-SCANNER FOR RADIOTHERAPY PROCEDURES

RELATED APPLICATION DATA

This application is a national phase application of International Application No. PCT/EP2015/064376 filed on Jun. 25, 2015 and published in the English language.

TECHNICAL FIELD

The present invention relates to a computer implemented method for determining, with the help of a transportable CT-scanner, the position of a soft tissue body part within a patient's body positioned in a treatment position relative to a radiotherapy treatment device, and to a corresponding computer program and system.

SUMMARY

The present invention relates to the field of medicine and in particular to the use of beams, in particular radiation beams in order to treat parts of the body. Ionizing radiation is in particular used for this purpose. In particular, the treatment beam comprises or consists of ionizing radiation. The ionizing radiation comprises or consists of particles (for example sub atomic particles or ions) or electromagnetic waves which are energetic enough to detach electrons from atoms or molecules and so ionize them. The treatment beam, in particular the treatment radiation is in particular used in radiation therapy (also called radiotherapy), in particular in the field of oncology. For the treatment of cancer in particular, parts of the body comprising the tumor are treated by using ionizing radiation. The tumor is an example for a soft tissue body part to be treated, also called treatment body part. The treatment beam is preferably controlled to pass through the treatment body part.

The arrangement of beam positions comprises (in particular consists of) at least one beam position, in particular a discrete set of beam positions or a continuous multiplicity (manifold) of beam positions. During treatment, a treatment beam in particular adopts the beam positions defined by the arrangement sequentially in particular in case there is just one beam source to emit a treatment beam. If there are several beam sources, beam positions can also be adopted simultaneously by the several treatment beams during the treatment. The arrangement of the at least one beam position which defines the at least one beam position relative to the treatment device, in particular during (actual) treatment (in particular during a treatment session, which is also called a fraction) is called actual arrangement. In particular, the actual arrangement has a point of intersection in which all treatment beams (in case of more than one) of the actual arrangement intersect. In particular, the determined position is described relative to the position of the intersection point, for instance in a reference system which has the intersection point in its origin. The intersection point corresponds in particular to an isocenter of the treatment device.

In particular, there is a defined planned relative position between a planned relative position of the treatment body part and a planned arrangement of beam positions. In particular a treatment planning (performed by a treatment planning system before the treatment, for instance based on computed tomographic images (called planning CT images)) results in the planned relative position between the treatment body part and the planned arrangement. In particular the actual arrangement is set to comprise the same number of beam positions as the planned arrangement. In particular in case the planned arrangement comprises two or more beam positions, the relative positions between the beam positions is set to be identical in the planned arrangement and in the actual arrangement.

Usually, treatment planning images such as CT images on which treatment planning is based, are taken at another place than that of radiotherapy, wherein the patient at first rests on a patient couch assigned to a CT scanner. After the planning CT-images have been taken and treatment planning has finished, the patient will then be placed on a patient couch assigned to a treatment device such as a LINAC. Often it is even so that a considerable period of time passes after the images the treatment planning is based on are taken, before radiotherapy is started.

Usually it is assumed that the spatial relationship between soft tissue and bony structures which may be both be visualized in a CT-image remains constant irrespective of the patient's position or state of motion. When the patient has been placed in position for radiotherapy, for example on a couch or a radiotherapy treatment device, x-ray images are then taken of the patient's body and the position of the bony structure is compared with a position of the treatment beam based on the information of the spatial relationship between the soft tissue and the bony structures, the spatial relationship between the soft tissue and the treatment beam can thus be established. Thereby, a shift in the position of the soft tissue relative to the position of the treatment beam can be determined and the patient can be moved correspondingly such that the patient is correctly positioned relative to the treatment beam such that the desired soft tissue be irradiated with treatment radiation.

However, such an approach can lead to a positional offset of the soft tissue from the desired position as the precise spatial relationship between the bony structures visualized by x-ray imaging and the soft tissue may not be known. In particular, the soft tissue may, for example due to its elastic properties have changed its spatial properties (in particular, size and/or shape) such that it is no longer covered by the treatment beam and the desired manner.

It is an object of the present invention to determine the current position of a soft tissue body part to be treated by radiotherapy, i.e. the position of a treatment body part of a patient being ready for radiotherapy and positioned on a patient couch of a treatment device.

This object is solved by the method, the program and the system according operating table the present invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention in particular provides a data processing method performed by a computer for determining the position of a soft tissue body part within a patient's body, which is to be treated by radiotherapy with a treatment beam arrangement of at least one position of a treatment beam issued by a treatment device, the data processing method comprising the following steps: acquiring CT-image data comprising information about the position of the body part within a coordinate system assigned to a transportable CT-device, wherein the patient's body is positioned relative in a treatment position to the treatment device, and wherein the CT-device is configured to be positioned relative to the patient's body and/or relative to the treatment device; acquiring first transformation data comprising information about a first transformation between the coordinate system assigned to the CT-device and a coordinate system assigned to the treatment device; determining, based on the CT-image data and the first transformation data, position data comprising information about the position of the body part within the coordinate system assigned to the treatment device.

In other words, at least one CT-image of the patient lying on a patient couch of the treatment device is made, wherein the treatment device may be a LINAC used for radiotherapy. Since the patient will remain on the patient couch during the radiotherapy procedure, no substantial positional change of the treatment body part within the patient is to be expected. The position of this target derived from the CT-images will therefore describe the target position during radiotherapy. Since the CT-image refers to the coordinate system of the transportable CT-device, the coordinates of the target have to be transferred into the coordinate system of the treatment device.

Providing CT-images of the patient resting on the patient couch of the radiotherapy treatment device offers, compared to known imaging approaches performed for radiotherapy, a range of advantages, comprising the following:
- improved soft tissue contrast compared to Cone Beam CT-images;
- provision of Hounsfields-Units which are crucial for planning the radiation dose;
- improved field-of-view;
- reduced image-acquisition-time;
- provision of four-dimensional image data for radiotherapy, which enables the consideration of time-dependent positions of anatomical structures, particularly the consideration of respiration cycles of the patient during a treatment session, which in turn may be considered for controlling/gating the treatment beam. Tracking of the patient's respiration curve may also imply the use of thermographic camera capturing live thermal images of the patient.

It is important to note that the CT-device according to the present invention is transportable and can therefore be freely moved relative to both, the treatment device and the patient couch supporting the patient in a treatment position. In particular, the transportable CT-device can, when not used during a radiotherapy procedure, be stored in a simulation room provided for CT-planning-procedures and/or for diagnostic purposes, which is located away from the treatment theater within which the patient receives radiotherapy. By doing so, different procedures on different patients which may even be performed simultaneously may have access to a CT-device without the need of a patient transport. In order to enable transport of the CT-device between the simulation or diagnostic site and a treatment site, the CT-device may comprise an undercarriage by which it can be freely moved in two dimensions on the floor of a hospital.

Since the transportable CT-device can be freely moved in two dimensions, it is crucial to know the exact relative position of the CT-device and the treatment device when the CT-images are made so that the coordinates of the target acquired within the coordinate system assigned to the CT-device can be transformed into the coordinate system assigned to the treatment device. Such transformation can also take into account an offset of the isocenter of the treatment device, which may occur after a certain period of time. For example, if a certain offset of the isocenter is determined by known procedures, such as the Winston-Lutz-test, that offset can be compensated for by an appropriate alteration of the coordinate transformation.

For this purpose, acquiring said first transformation data may involve using a position detection unit configured to determine the spatial position of the CT-device with respect to the treatment device, particularly wherein the position detection unit comprises at least one element selected from the group consisting of an optical tracking system; an EM-tracking system; an ultrasound tracking system; and a sensor assigned to an actuating element configured to induce a transport movement of the CT-device, the sensor being configured to determine the current position of the actuating element relative to a known initial position of the actuating element; a sensor device, particularly a camera, assigned to the CT-device (3) and configured to detect markings that define the guiding path; a tracking system comprising a 3D-range camera configured to determine three-dimensional surface structures.

In particular, it is conceivable to utilize a tracking system that is assigned to the treatment device and that is provided in a fixed position relative to the treatment device. To enable a positional tracking by the tracking system, the CT-device may comprise at least one tracking marker configured to be detected by the tracking system. Further, the tracking system may be an optical tracking system, which may in particular detect signals within the infrared range of light, or may as well be an EM tracking system or even an ultrasound tracking system. Further, the CT-device may comprise at least one sensor which is configured to determine the current position of at least one of the wheels of the undercarriage with respect to an initial position thereof, which is known to the position detection unit. By doing so, the current position of the CT-device can be calculated. It is also conceivable that a 3D-range camera is utilized, which is configured to determine three-dimensional surface structures. Such 3D-range camera together with known data as to the three-dimensional surfaces of the devices provided at the treatment site enable determining the current spatial position of said devices relative to each other.

Moreover, acquiring said first transformation data may involve using a guiding unit configured to guide the CT-device along a path between a first position of the CT-device and a second position of the CT-device allowing for acquiring the CT image data, particularly wherein the guiding unit, just like the position detection unit described above, is configured to determine the spatial position of the CT-device with respect to the treatment device, and/or wherein the second position is predefined with respect to the treatment device, and/or wherein the guiding unit comprises at least one element selected from the group consisting of: an induction loop defining the guiding path; a sensor device, particularly a camera, assigned to the CT-device and configured to detect markings that define the guiding path; a transmitter emitting electromagnetic radiation, and a complementary receiver receiving said electromagnetic radiation, wherein the transmitter or the receiver is mounted to the CT-device, allowing the guiding unit to determine the path to the second position; a mechanical coupling defining a coupling position of the CT-device with respect to the treatment device.

As the CT-device is freely movable in two dimensions, it is desirable to have assistance in positioning the CT-device with respect to the patient/patient couch and to the treatment device. It is conceivable that a predefined path is defined, starting from a predefined parking or storage position for the CT-device, and running to a position at which the CT-device can take CT-images of the patient. For example, an initial parking position for the CT-device can be marked up for medical personnel to bring the CT-device into an initial position. From there on the guiding unit may take over, so that the CT-device can automatically travel from the initial parking position into a final position which allows for acquiring CT-image data.

With the final second position of the CT-device known with respect to the treatment device, a transformation of the coordinates of structures as seen in the images taken at the second position into the coordinate system of the treatment device is possible.

Additionally or alternatively to the position detection unit and/or the guiding unit, the inventive method may further comprise the steps of: acquiring positioning-image data comprising information about the position of the body part relative to the treatment device; determining, based on the positioning-image data and the CT-image data, said first transformation data; wherein a positioning imaging device, particularly an X-ray imaging device, assigned to the treatment device is used to acquire the positioning image data, and wherein the positioning image data is registered with the CT-image data.

In case the positioning imaging device is provided in a known and invariant position relative to the treatment device, the images made by the positioning imaging device allow to derive the three dimensional coordinates of each structure seen in the images within the coordinate system of the treatment device. A following registration of the positioning images made by the positioning imaging device and any CT-images made by the CT-device will then enable a transformation of the position of any structures seen in the CT-images into the coordinate system of the treatment device.

With such image registration it is not even necessary to know the exact position of the CT-device relative to the treatment device and it would be sufficient that the CT-device is positioned coarsely relative to the treatment device. On the other hand, the position detection unit and/or the guiding unit may be configured to determine the position of the CT-device relative to the treatment device at such high accuracy, that an image registration as described above is not necessary for a coordinate transformation from the CT-device-coordinate system to the treatment device-coordinate system.

It becomes apparent that the method as described above provides highly topical CT-image data of a patient positioned with respect to a radiotherapy treatment device. The present invention therefore also allows for determining whether previously acquired image data is still valid for the patient lying on the treatment patient couch. For this purpose, the inventive method may further comprise the steps of: acquiring, particularly with the patient's body taking a position being different from a treatment position relative to the treatment device, planning-CT image data comprising information about the position of the body part; acquiring second transformation data comprising information about a second transformation between the coordinate system assigned to the planning-CT image data and a coordinate system assigned to the treatment device; determining, based on said second transformation data, said planning-CT image data and said CT-image data, consistency data comprising information about whether the positional registration of the soft tissue body part based on said planning-CT image data is valid for the patient's body taking the treatment position relative to the treatment device.

In particular, it can be for example verified whether the target position as determined on the basis of planning-CT-images beforehand is still correct and can be used for resetting the isocenter of the radiotherapy treatment device. In case the target position has changed in the meantime, the planning-CT-images may be replaced by the current CT-images acquired with the help of the transportable CT-device, and the treatment procedure may be performed on the basis of the updated positional data derived from the current images.

It is also conceivable that CT-image data is acquired several times during the radiotherapy procedure with the help of the transportable CT-device so as to consecutively update the image data of the patient. In this context, the CT-device may travel back and forth between a first position spaced apart from the treatment site and a second position which allows for acquiring CT-image data. By doing so, the patient image data can be updated as often as desired and radiotherapy can be performed on the basis of the latest positioned data. Further, it is conceivable that the CT-device is reproducibly placed at the same position relative to the treatment device, for example with the help of the position detection unit and/or the guiding unit, so that the necessary transformation from the coordinate system of the CT-device to the coordinate system of the imaging device is already known and does not have to be calculated for each of the CT-images acquired later on.

However, the planning CT-image data, as long as it is acquired with a CT-imaging device the position of which has not been determined with respect to the treatment device, has to be transformed from a coordinate system assigned to the planning CT-image to the coordinate system assigned to the treatment device. This may be done by registering the planning CT-image data with the CT-image data acquired by the transportable CT-device. Additionally or alternatively, the planning CT-image data may as well be registered with the positioning image data which already refers to the coordinate system of the treatment device.

Regarding the registration of CT-images, it is not even necessary to perform a coordinate-transformation between the CT-device coordinate system and the treatment device coordinate system. For example, the CT-images made by the transporter CT-device may be registered, particularly using an image registration, with any images the position of which is known within the coordinate system of the treatment device. This may be in particular desirable for updating a treatment plan that is based on an older CT-image. In this context, the transportable CT-device may be used as described herein, but without transforming positional data from the CT-device-coordinate system.

Since treatment plans for radiotherapy are usually based on CT-image data acquired long before the patient is placed on the patient couch of the treatment device, the present invention may also provide for an update of such treatment plan. Therefore, the inventive method may further comprise the steps of: acquiring treatment constraints data comprising information about treatment constraints for radiotherapy of the body part with the treatment beam arrangement, the treatment constraints being in particular defined on the basis of the planning-CT image data; determining, based on the treatment constraints data and the consistency data, constraint consistency data comprising information about whether the treatment constraints are fulfilled for the patient's body taking the treatment position relative to the treatment device.

For example, the treatment plan may require that certain parts of the patient's body must not be irradiated by the treatment beam. As the relative position of the target to be irradiated and the body parts to be avoided by the treatment beam is determined on the basis of planning CT-image data, CT-images made of the patient positioned on the treatment couch also allow for an update of the treatment plan, i.e. it can be checked on the basis of the updated CT-images whether the treatment plan is still valid and the set constraints are still fulfilled for the patient placed on the treatment couch. Otherwise, the treatment plan can be updated with the constraints adapted to the data derived from the current CT-images. Further, it is also conceivable that the treatment plan is consecutively updated during a radiotherapy procedure with the help of a plurality of consecutively acquired CT-image data, wherein the patient remains on the treatment couch of the treatment device (online update of the treatment plan), so that the updated treatment plan is applied immediately for the current radiotherapy procedure.

It is further conceivable that registering the positioning image data with the CT-image data and/or, registering the positioning image data with the planning-CT image data and/or, registering the CT-image data with the planning-CT image data involves an image registration procedure, particularly based identifying bony structures of the patient's body in the image data to be registered.

It is further conceivable that registering image data involves an elastic image fusion. Alternatively or additionally, registering image data may also involve a rigid image fusion.

Since the available space for placing the transportable CT-device in the vicinity of the treatment location is quite confined, the inventive method may also provide for positioning the CT-device with respect to the treatment device and/or the patient couch supporting the patient. This will help in preventing collisions between the CT-device and/or the patient couch/the patient. The inventive method may therefore comprise the steps of acquiring imaging-arrangement data including information about a spatial arrangement of the body part, the treatment device and the transportable CT-device, the spatial arrangement allowing for acquiring CT image data of the body part with the patient's body positioned on a patient couch of the treatment device; acquiring current-arrangement data including information about a current spatial arrangement of the body part, the treatment device and the transportable CT-device; determining, based on the imaging-arrangement data and the current-arrangement data, rearrangement data including information about a rearrangement of the body part, the treatment device and/or the transportable CT-device, to reach the spatial arrangement allowing for acquiring CT image data.

With the current arrangement and the desired arrangement of the patient couch, the treatment device and the CT-device known, it is possible to provide actuator means or medical personnel with information as to necessary positional changes so as to reach the desired arrangement allowing for acquiring CT-images of the patient. For example, the patient couch can be rotated automatically or manually around a vertical axis so that the CT-device can be moved closely to the head-end of the patient couch so as to acquire CT-image data of the patient's head. Further, it may be necessary to tilt the accelerator-head of the radiotherapy treatment device so as to gain space for the gantry of the CT-device placed around the patient.

It is either possible to transmit rearrangement data, i.e. data describing necessary changes in the positional arrangement of the patient couch, the treatment device and/or the CT-device, to at least one repositioning unit which may then automatically reposition the treatment device, the CT-device and/or the patient couch together with the patient's body. Additionally or alternatively, it is possible to transmit that rearrangement data to an output unit such as a computer monitor configured to provide information to medical personnel regarding a necessary rearrangement of the treatment device, the CT-device and/or the patient couch together with the patient's body.

A further aspect of the present invention relates to a system for determining the position of a soft tissue body part within a patient's body, which is to be treated by radiotherapy with a treatment beam arrangement of at least one position of a treatment beam issued by a treatment device, comprising: a treatment device configured to issue the treatment beam arrangement; a patient couch configured to support a patient's body during radiotherapy; a transportable CT-device configured to be transported to a radiotherapy treatment site, to be moved relative to the treatment device and/or the patient couch, and to acquire CT-image data of the patient's body.

Further, that system may comprise at least one element selected from the group consisting of a repositioning unit configured to reposition the patient couch, the treatment device and/or the transportable CT-device so as to reach the spatial arrangement allowing for acquiring CT image data; a guiding unit configured to guide the CT-device along a path between a first position of the CT-device and a second position of the CT-device allowing for acquiring the CT image data, particularly wherein the guiding unit is configured to determine the spatial position of the CT-device with respect to the treatment device, and/or wherein the second position is predefined with respect to the treatment device, a positioning image device assigned to the treatment device, and provided in a known spatial position relative to the treatment device, particularly configured to create X-ray images; a position detection unit configured to determine the spatial position of the CT-device with respect to the treatment device; a computer configured to perform any data processing method described herein.

Each of the elements of the system as described above may be configured to allow for the data processing method described further above to perform any method steps involving the corresponding element or elements.

A further aspect of the present invention relates to a corresponding computer program which, when running on a computer, causes the computer to perform the method steps of any method described herein, and/or a program storage medium on which the program is stored, in particular, in a non-transitory form.

The present invention also relates to a corresponding system as described herein, comprising a computer on which such program is stored and/or run.

Definitions

The method in accordance with the invention is for example a computer implemented method. For example, all the steps or merely some of the steps (i.e. less than the total number of steps) of the method in accordance with the invention can be executed by a computer. An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or vithe interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one coordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium.

The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a tracking marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Preferably, atlas data is acquired which describes (for example defines, more particularly represents and/or is) a general three-dimensional shape of the anatomical body part. The atlas dattherefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas dattherefore represents the result of a statistical analysis of such medical image data for a plurality of human bodies. This result can be output as an image—the atlas dattherefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionizing radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its coordinates in a defined coordinate system. The specific location is a point, preferably a point on a straight line. This line is then referred to as a "beam line" and extends in the beam direction, for example along the central axis of the treatment beam. The defined coordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there are a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention can in particular involve the use of Airo® and ExacTrac®, both products of Brainlab® AG, Germany.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
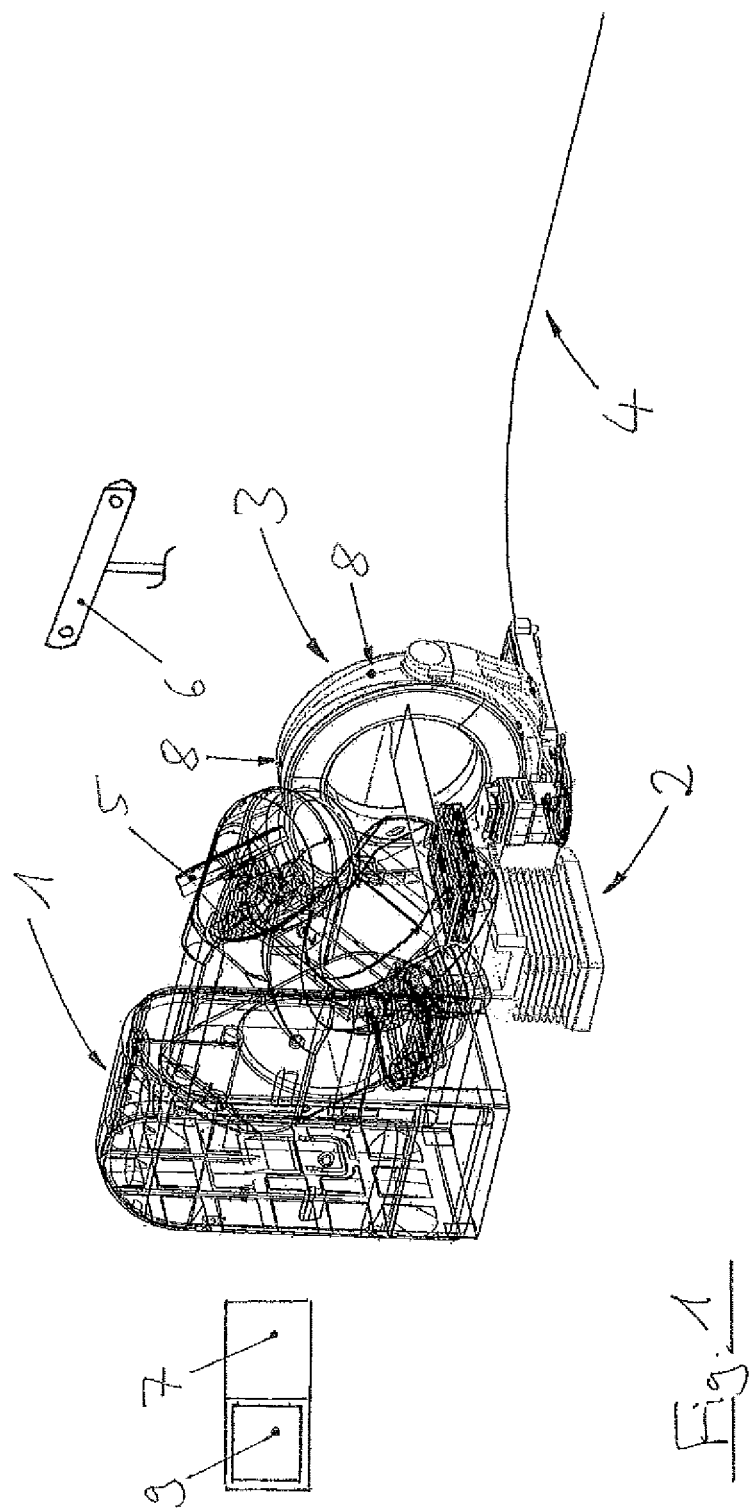
FIG. 1 shows a system according to the present invention comprising a treatment device, a patient couch and a transportable CT-device.

FIG. 1 shows a radiotherapy system in accordance with the present invention comprising a transportable, i.e. freely movable CT-scanner 3. The radiotherapy system further comprises a conventional treatment device 1 comprising a linear accelerator (LINAC) emitting a treatment beam which is to irradiate a target within a patient's body lying on the treatment couch 2 of the treatment device 1.

In case updated CT-images have to be acquired with a patient lying on the patient couch 2, particularly right before or after a target of the patient's body is irradiated, the patient couch is rotated around a vertical axis to a position shown in FIG. 1. To gain maneuvering space for the circular gantry of the transportable CT-device 3, the accelerator head of the treatment device 1 can be tilted, as this is shown in FIG. 1, away from the location the CT-device 3 is planned to be positioned for acquiring CT-images of the patient. Moreover, the patient couch 2 can be moved relative to its base and away from the accelerator head of the treatment device 1.

After the treatment device 1 and the patient couch 2 are positioned to allow the CT-device to take at least one CT-image of the patient, the CT-device 3 is moved to a predetermined position relative to the treatment device 1 and the patient couch 2. For this purpose, an induction loop defines a predetermined path from an initial parking position (not shown in FIG. 1) in which the CT-device 2 can be manually brought by medical personnel after it has been used elsewhere. Starting from that parking position, the CT-device automatically moves along the path defined by an induction loop 4 of a guiding unit to its final position next to the patient couch 2.

Further, the system comprises an optical tracking system 6 having a camera array configured to identify the optical tracking markers 8 which are attached to the gantry of the CT-device 3. Since the camera array is provided in a predetermined positional arrangement relative to the treatment device 1, the position of the tracking markers 8 and therefore also the position of the CT-device 3 can be determined relative to the treatment device 1. Based on this relative position, any positional data derived from images acquired by the CT-device 3 can then be transformed into the coordinate system of the treatment device 1.

In the alternative, the induction loop 4 may be for example replaced by an array of optical tracking markers that would allow a tracking camera mounted to the CT-device to accurately determine the position of the CT-device 3 relative to the treatment device 1.

Provided that this relative position can be determined by the guiding unit with sufficient accuracy, the optical tracking system 6 may be omitted, but may also remain as a redundant system for determining the position of the CT-device 3.

A further possibility to transfer positional data from the coordinate system of the CT-device 3 to the coordinate system of the treatment device 1 is enabled by the positioning imaging device 5 that takes x-ray-images of the patient lying on the treatment couch 2. These x-ray-images have been acquired with respect to the coordinate system of the imaging device 1 and may be registered to the CT-images taken by the CT-device 3. The image registration will then allow for a transformation of any positional data derived from the CT-images into the coordinate system of the treatment device 1.

Further, the system comprises a computer 7 that provides the computing power necessary to perform the method steps as referred to above, and which is connected via at least one data link with the remaining components of the system shown in FIG. 1. A computer monitor 9 connected to the computer 7 may provide a user interface, that may in particular help medical personnel to manually move (in case it is desired not to use the induction loop 4 to automatically position the CT-device 3) the CT-device 3 next to the patient couch 2 for taking CT-images of the patient.

Figure 2:
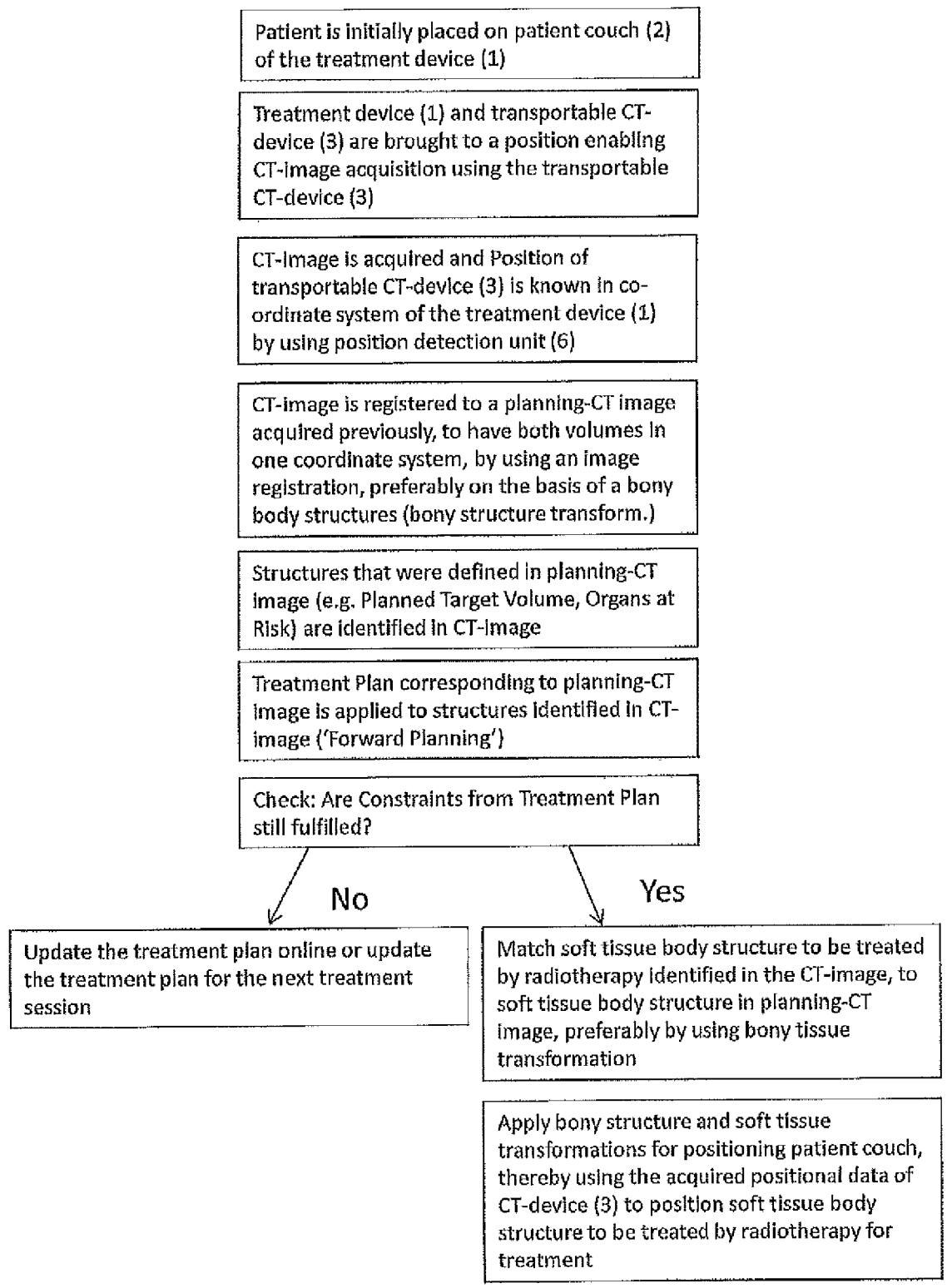
FIG. 2 shows a first example of a process sequence according to the present invention.
Figure 3:
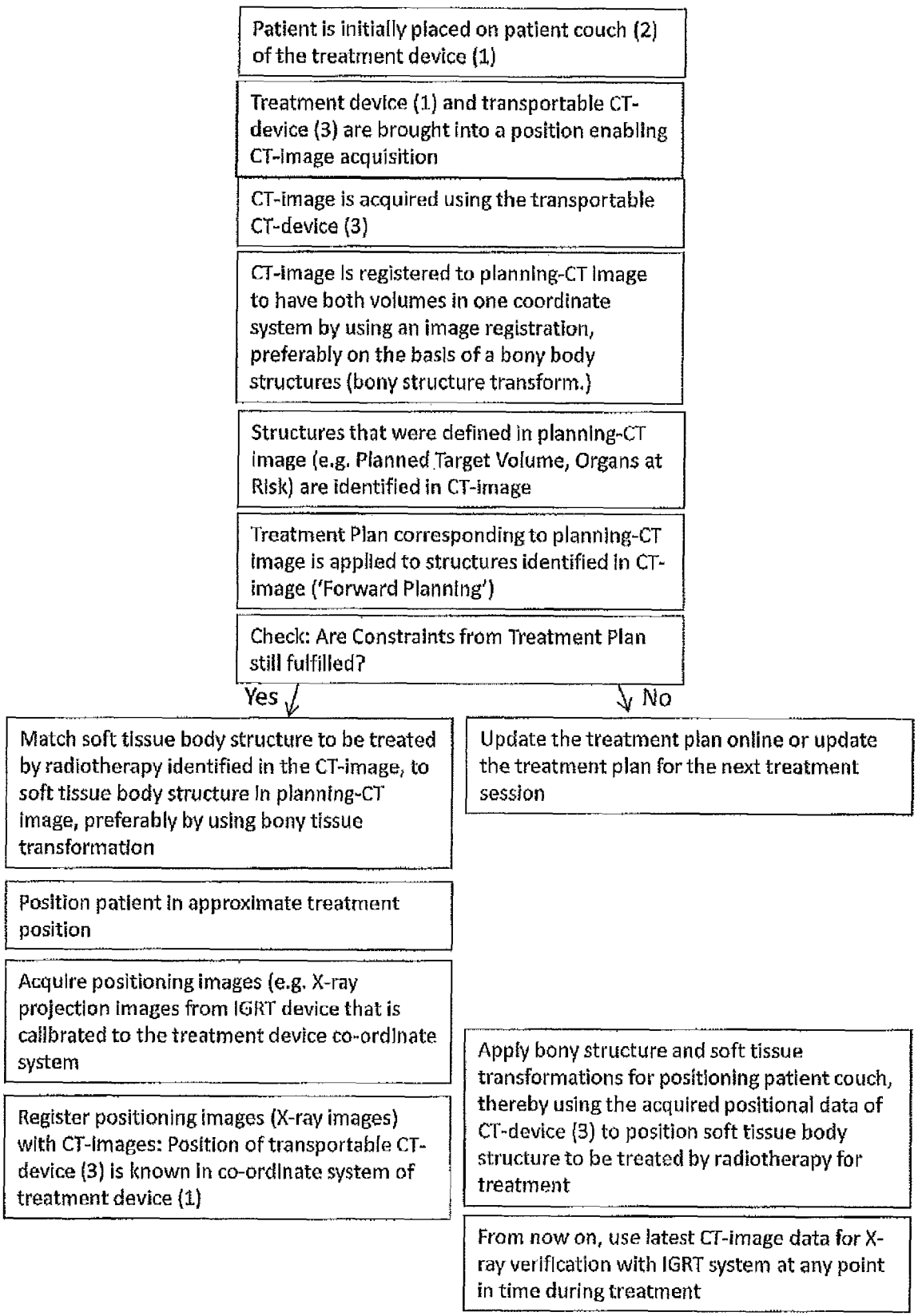
FIG. 3 shows a second example of a process sequence in accordance with the present invention.

FIGS. 2 and 3 show two examples for a process sequence in accordance with the inventive method and are self-explanatory.

The invention claimed is:

1. A data processing system comprising at least one computer having at least one processor configured to execute a computer-implemented medical data processing method for determining a position of a soft tissue body part within a patient's body, which is to be treated by radiotherapy with a treatment beam arrangement of at least one position of a treatment beam issued by a treatment device, the at least one processor executing the steps of:

a. acquiring, at the at least one processor, planning computed tomography image (planning-CT-image) data showing information about the position of the soft tissue body part;
   b. acquiring, at the at least one processor, positioning-image data comprising information about the position of the soft tissue body part within a coordinate system assigned to the treatment device;
   c. acquiring, at the at least one processor, computed tomography image (CT-image) data comprising information about the position of the soft tissue body part within a coordinate system assigned to a transportable computed tomography device (CT-device) having an undercarriage by which the CT-device can be freely moved in multiple directions on a floor of a medical treatment area, wherein the patient's body is positioned in a treatment position relative to the treatment device, and wherein the CT-device is configured to be positioned relative to the patient's body and/or relative to the treatment device;
   d. determining, at the at least one processor, first registration data comprising information about a position of the coordinate system assigned to the CT-device with respect to the coordinate system assigned to the treatment device, wherein determining the first registration data includes registering the CT-image data with the positioning-image data via a first image fusion;
   e. determining, at the at least one processor, second registration data comprising information about the position of the soft tissue body part as shown by the planning-CT-image data with respect to the coordinate system assigned to the treatment device, wherein determining the second registration data includes registering the planning-CT-image data with the positioning-image data via a second image fusion;
   f. determining, by the at least one processor and based on the first registration data and the second registration data, relative position data comprising information about relative position between the soft tissue body part as shown by the planning-CT-image data and the soft tissue body part as shown by the CT-image data and within the coordinate system assigned to the treatment device; and
   g. determining, by the at least one processor and based on the CT-image data, the planning-CT-image data and the second registration data, consistency data comprising information about whether positional registration of the soft tissue body part based on the planning-CT-image data is valid for the patient's body taking the treatment position relative to the treatment device.

2. A computer-implemented medical data processing method for determining a position of a soft tissue body part within a patient's body, which is to be treated by radiotherapy with a treatment beam arrangement of at least one position of a treatment beam issued by a treatment device, the method comprising executing, on at least one processor of at least one computer the steps of:

a. acquiring, at the at least one processor, planning computed tomography image (planning-CT-image) data showing information about the position of the soft tissue body part;
   b. acquiring, at the at least one processor, positioning-image data comprising information about the position of the soft tissue body part within a coordinate system assigned to the treatment device;
   c. acquiring, at the at least one processor, computed tomography image (CT-image) data comprising information about the position of the soft tissue body part within a coordinate system assigned to a transportable computed tomography image (CT-device) having an undercarriage by which the CT-device can be freely moved in multiple directions on a floor of a medical treatment area, wherein the patient's body is positioned in a treatment position relative to the treatment device, and wherein the CT-device is configured to be positioned relative to the patient's body and/or relative to the treatment device;

d. acquiring, at the at least one processor, first registration data comprising information about a position of the coordinate system assigned to the CT-device with respect to the coordinate system assigned to the treatment device, wherein acquiring the first registration data includes registering the CT-image data with the positioning-image data via a first image fusion;

e. acquiring, at the at least one processor, second registration data comprising information about the position of the soft tissue body part as shown by the planning-CT-image data with respect to the coordinate system assigned to the treatment device, wherein acquiring the second registration data includes registering the planning-CT-image data with the positioning-image data via a second image fusion;

f. determining, by the at least one processor and based on the first registration data and the second registration data, relative position data comprising information about relative position between the soft tissue body part as shown by the planning-CT-image data and the soft tissue body part as shown by the CT-image data and within the coordinate system assigned to the treatment device; and g. determining, by the at least one processor and based on the CT-image data, the planning-CT-image data and the second registration data, consistency data comprising information about whether positional registration of the soft tissue body part based on the planning-CT-image data is valid for the patient's body taking the treatment position relative to the treatment device.

3. The data processing method according to claim 2, wherein acquiring the first registration data includes using a position detection unit configured to determine a spatial position of the CT-device with respect to the treatment device, wherein the position detection unit comprises at least one element selected from the group consisting of:

an optical tracking system;
an electromagnetic tracking (EM-tracking) system;
an ultrasound tracking system;
a sensor assigned to an actuating element configured to induce a transport movement of the CT-device, the sensor being configured to determine a current position of the actuating element relative to a known initial position of the actuating element;
a sensor device assigned to the CT-device and configured to detect markings that define a guiding path;
a tracking system comprising three-dimensional range camera configured to determine three-dimensional surface structure.

4. The data processing method according to claim 2, further comprising a positioning imaging device assigned to the treatment device which is used to acquire the positioning-image data, and wherein the positioning imaging device is an X-ray imaging device.

5. The data processing method according to claim 2, further comprising:

acquiring, at the at least one processor, treatment constraints data comprising information about treatment constraints for radiotherapy of the body part with the treatment beam arrangement, the treatment constraints being defined on a basis of the planning-CT-image data; and determining, by the at least one processor and based on the treatment constraints data and the consistency data, constraint consistency data comprising information about whether the treatment constraints are fulfilled for the patient's body taking the treatment position relative to the treatment device.

6. The data processing method according to claim 2, further comprising:

acquiring, at the at least one processor, imaging-arrangement data including information about a spatial arrangement of the soft tissue body part, the treatment device and the CT-device, the spatial arrangement allowing for acquiring CT-image data of the soft tissue body part within the patient's body positioned on a patient couch of the treatment device;

acquiring, at the at least one processor, current-arrangement data including information about a current spatial arrangement of the soft tissue body part, the treatment device and the CT-device;

determining, by the at least one processor and based on the imaging-arrangement data and the current-arrangement data, rearrangement data including information about a rearrangement of the soft tissue body part, the treatment device and/or the CT-device, to reach the spatial arrangement allowing for acquiring CT-image data.

7. The data processing method according to claim 6, wherein the rearrangement data provides the information which is used to automatically reposition the patient's body, the treatment device or the CT-device.

8. The data processing method according to claim 2, further comprising a guiding unit is configured to determine a spatial position of the CT-device with respect to the treatment device, wherein the guiding unit is configured to guide the CT-device along a guiding path between a first position of the CT-device and a second position of the CT-device allowing for acquiring the CT image data.

9. The data processing method according to claim 8, wherein the guiding unit comprises at least one element selected from the group consisting of:

an induction loop defining the guiding path;
a sensor device assigned to the CT-device and configured to detect markings that defines the guiding path;
a transmitter emitting electromagnetic radiation, and a complementary receiver receiving said electromagnetic radiation, wherein the transmitter or the receiver is mounted to the CT-device, allowing the guiding unit to determine the guiding path to the second position; or
a mechanical coupling defining a coupling position of the CT-device with respect to the treatment device.

10. The data processing method according to claim 8, further comprising registering the CT-image data with the planning-CT-image data via an image registration procedure.

11. The data processing method according to claim 10, wherein registering the CT-image data with the planning-CT-image data includes an elastic image fusion.

12. The data processing method according to claim 10, further comprising transmitting rearrangement data to an output unit which is configured to provide rearrangement information to medical personnel regarding a necessary rearrangement of the patient's body, the treatment device and/or the CT-device.

13. A data processing system comprising at least one computer having at least one processor configured to execute a computer-implemented medical data processing method for determining a position of a soft tissue body part within a patient's body, which is to be treated by radiotherapy with a treatment beam arrangement of at least one position of a treatment beam issued by a treatment device, the at least one processor executing the steps of:

a. acquiring, at the at least one processor, planning computed tomography image (planning-CT-image) data showing information about the position of the soft tissue body part;

b. acquiring, at the at least one processor, positioning-image data comprising information about the position of the soft tissue body part within a coordinate system assigned to the treatment device;

c. acquiring, at the at least one processor, computed tomography image (CT-image) data comprising information about the position of the soft tissue body part within a coordinate system assigned to a transportable computed tomography device (CT-device) having an undercarriage by which the CT-device can be freely moved in multiple directions on a floor of a medical treatment area, wherein the patient's body is positioned in a treatment position relative to the treatment device, and wherein the CT-device is configured to be positioned relative to the patient's body and/or relative to the treatment device;

d. determining, at the at least one processor, first registration data comprising information about a position of the coordinate system assigned to the CT-device with respect to the coordinate system assigned to the treatment device, wherein determining the first registration data includes registering the CT-image data with the positioning-image data via a first image fusion;

e. determining, by the at least one processor, second registration data comprising information about the position of the soft tissue body part as shown by the planning-CT-image data with respect to the coordinate system assigned to the treatment device, wherein determining the second registration data includes registering the planning-CT-image data with the positioning-image data via a second image fusion; and f. determining, by the at least one processor and based on the first registration data and the second registration data, relative position data comprising information about relative position between the soft tissue body part as shown by the planning-CT-image data and the soft tissue body part as shown by the CT-image data and within the coordinate system assigned to the treatment device, g. determining, by a guiding unit, a spatial position of the CT-device with respect to the treatment device, and guiding the CT-device, by the guiding unit, along a path between a first position of the CT-device and a second position of the CT-device allowing for acquiring the CT image data.

* * * * *